United States Patent
Carullo, Jr. et al.

(10) Patent No.: US 7,258,695 B2
(45) Date of Patent: Aug. 21, 2007

(54) HAIR RESTORATION DEVICE AND METHODS OF USING AND MANUFACTURING THE SAME

(75) Inventors: John F. Carullo, Jr., Dallas, TX (US); Charles E. Maricle, Houston, TX (US)

(73) Assignee: Sonetics International, Houston, TX (US)

( * ) Notice: Subject to any disclaimer, the term of this patent is extended or adjusted under 35 U.S.C. 154(b) by 0 days.

(21) Appl. No.: 11/053,715

(22) Filed: Feb. 8, 2005

(65) Prior Publication Data

US 2006/0178712 A1 Aug. 10, 2006

(51) Int. Cl.
*A61N 5/06* (2006.01)
*A61N 5/067* (2006.01)

(52) U.S. Cl. .......................................... 607/88; 607/89

(58) Field of Classification Search .................. 607/88, 607/89, 93, 94
See application file for complete search history.

(56) References Cited

U.S. PATENT DOCUMENTS

| | | | | |
|---|---|---|---|---|
| 2,688,971 A | * | 9/1954 | Daniels et al. ................. | 607/79 |
| 5,300,097 A | * | 4/1994 | Lerner et al. ................. | 607/93 |
| 5,595,437 A | * | 1/1997 | Rapisarda et al. .......... | 362/555 |
| 6,053,180 A | * | 4/2000 | Kwan .......................... | 132/232 |
| 6,106,294 A | * | 8/2000 | Daniel ......................... | 433/216 |
| 6,497,719 B2 | | 12/2002 | Pearl et al. | |
| 6,802,853 B1 | | 10/2004 | Osendowski | |
| 6,989,023 B2 | * | 1/2006 | Black ........................... | 607/90 |
| 7,194,316 B2 | * | 3/2007 | Bousfield et al. ............ | 607/150 |
| 2003/0093915 A1 | * | 5/2003 | Pearl et al. ..................... | 34/96 |
| 2004/0193236 A1 | * | 9/2004 | Altshuler et al. .............. | 607/88 |
| 2005/0137656 A1 | * | 6/2005 | Malak .......................... | 607/88 |

FOREIGN PATENT DOCUMENTS

| | | | |
|---|---|---|---|
| DE | 9102407.2 | * | 8/1997 |
| JP | 2-136146 | | 5/1990 |
| JP | 3-228708 | | 10/1991 |

* cited by examiner

*Primary Examiner*—Roy D. Gibson
(74) *Attorney, Agent, or Firm*—Donald J. Ersler

(57) ABSTRACT

The present invention provides for a hair restoration device and methods of manufacturing and using the same. In one embodiment, the hair restoration device is comprised of (i) a hairbrush body housing a plurality of wide-pattern laser LEDs configured to cooperate to project a precision laser light pattern at a focal plane proximate a skin area to be irradiated; and (ii) bristles extending from the hairbrush body and terminating substantially at the focal plane.

20 Claims, 3 Drawing Sheets

HAIR RESTORATION DEVICE AND METHODS OF USING AND MANUFACTURING THE SAME

TECHNICAL FIELD OF THE INVENTION

The present invention is directed, in general, to a hair restoration device and, more specifically, to a hairbrush housing a laser assembly of wide-pattern laser light emitting diodes (LEDs) projecting a focused precision light pattern directly on a skin area to be irradiated.

BACKGROUND OF THE INVENTION

Hair loss and graying are viewed as significant problems by a substantial percentage of the population. Older individuals view it as a sign of irreversible aging every time they look into a mirror or view a photograph of themselves. In the case of younger individuals, it makes them look much older than they are, or at least think they are, which distresses them and, in some cases, their spouses. A large number of these people will go to great lengths to stop or reverse the process of balding and graying. This is why, since time immemorial, numerous attempts have been made to improve a persons appearance by restoring the appearance of a full head of hair.

Notwithstanding the various creams and ointments peddled by so-called "patent medicine men", the earliest successful solutions typically involved various kinds of hair pieces. While wigs and toupees address the more obvious appearance concerns in most cases they also present obvious problems. Except for those that are exceptionally well made, a trained eye can usually detect that they are not real. In some cases, hair pieces are so notoriously badly made that they can easily be detected even by an untrained eye. Well made hair pieces are usually very expensive since they are generally made of human hair. They are made even more expensive by the fact that the hair color of the wearer must be closely matched. Hair pieces are also inconvenient because they usually have to be removed if a wearer wants to go swimming or engage is certain other athletic endeavors. They also frequently come off or get skewed when least expected. In addition to hair pieces, more complicated mechanical solutions to restore the appearance of having a full head of hair have been developed, such as hair weaving. These solutions are still quite expensive and frequently share the same problems as the more prevalent and conventional hair pieces.

A modern medical solution to hair loss is to surgically replace missing hair with hair plugs. This procedure overcomes some of the problems created by the use of hair pieces but creates its own entirely new set of problems. Because replacement hair plugs are from the individual being treated, the color will be correct and replacement hair will look natural, but this method of treating hair loss is still expensive because it involves a surgical procedure that must be done by, or under the supervision of, a physician.

Other solutions to baldness and hair loss involve various modern drugs, which can take the form of either an ingestible medication or a topical ointment. Because the more effective products must be prescribed by a physician, they are expensive. The over the counter products are usually much weaker than the prescription products and, thus, are not as effective. In addition, some of these drugs have the potential of causing harmful side effects, such as liver damage.

It is now believed that lasers can be used to stimulate hair growth. To this end, various laser devices to stimulate hair growth have been developed. These laser devices generally have the appearance of the large permanent hair dryers seen in a beauty shop, with floor or chair mounted helmets. Such devices contain multiple laser assemblies and are designed to irradiate an individual's entire scalp and hair with laser energy. The main disadvantage of such devices is that they are large and pretty much permanently installed. This means that a user must travel to the facility having the devices in order to obtain the desired treatment. These treatments are usually paid for on a per treatment basis, which can make the total cost quite expensive. Such treatments can represent a major inconvenience for a user as well as a substantial financial commitment.

Accordingly, what is needed in the art is a small portable, easy-to-use, relatively inexpensive laser device that an individual can use at his or her convenience.

SUMMARY OF THE INVENTION

To address the above-discussed deficiencies of the prior art, the present invention provides for a hair restoration device and methods of manufacturing and using the same. In one embodiment, the hair restoration device is comprised of (i) a hairbrush body housing a plurality of wide-pattern laser LEDs configured to cooperate to project a precision laser light pattern at a focal plane proximate a skin area to be irradiated; and (ii) bristles extending from the hairbrush body and terminating substantially at the focal plane.

Thus the present invention provides a compact, lightweight, easy-to-use, safe device for hair restoration using proven technology with respect to both hair growth and color. The device is embedded within a familiar hairbrush and has a plurality of laser LEDs that provide a precision pattern of laser light. The bristles are constructed to focus the laser light at a focal plane that coincides with a user's skin or scalp (herein synonymous) when the brush is used.

In one embodiment, each of the wide pattern laser LEDs in the body of the hair restoration device projects an elliptical laser light shape on the focal plane. A further refinement of this embodiment provides for the laser LEDs to be positioned so that the elliptical laser light shapes cooperate to form a precise laser light pattern to provide complete coverage of an area of skin or scalp to be irradiated without leaving any gaps or holes. A particularly useful embodiment, provides for the laser LEDs to be arranged so that each elliptical laser light shape is diagonal to the major axis of the hairbrush body.

An advantageous embodiment provides for the laser LEDs in the hair restoration device to be powered by a battery power supply housed within the hairbrush body. In another embodiment, the battery power supply is rechargeable. These embodiments offer complete independence to a user who can virtually use the device anywhere at any time.

In another useful embodiment of the invention the hair restoration device has an interchangeable LED head. This embodiment permits the use of non-laser LED heads housing LEDs emitting light having a wavelength of between about 235 nanometers and about 1180 nanometers.

Because the bristles of the device terminate substantially at the focal plane of the light emitted by the LEDs, a useful embodiment provides for the use of stiff bristles. These serve to keep the laser light pattern optimally focused when in use so as to obtain the most favorable results.

Although the hair restoration device can be constructed from any material and be within the intended scope of the present invention, plastic is a particularly useful material to use in making the device. Plastic provides several advantages, including light weight, ease of manufacture, and electrically non-conductive. Therefore, one embodiment of the present invention provides for the hairbrush body to be plastic.

The invention also provides for methods of using and manufacturing a hair restoration device. One embodiment to manufacture a restoration device provides for; (i) a plurality of wide-pattern laser LEDs to be located within a hairbrush body, which LEDs are configured to cooperatively project a precision laser light pattern at a focal plane proximate a skin area to be irradiated; and (ii) bristles located on the hairbrush body that extend and terminate substantially at the focal plane. Other embodiments to manufacture the hair restoration device will be readily understood by those of ordinary skill in the pertinent art from the descriptions of the invention herein set forth.

The invention also provides various embodiments for using the hair restoration device described herein. These embodiments will be readily understood by those of ordinary skill in the art from the descriptions of the invention herein set forth.

The foregoing has outlined preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention. Those skilled in the art should also realize that such equivalent constructions do not depart from the spirit and scope of the invention.

BRIEF DESCRIPTION OF THE DRAWINGS

For a more complete understanding of the invention, reference is now made to the following descriptions taken in conjunction with the accompanying drawing, in which.

DETAILED DESCRIPTION

Figure 1:
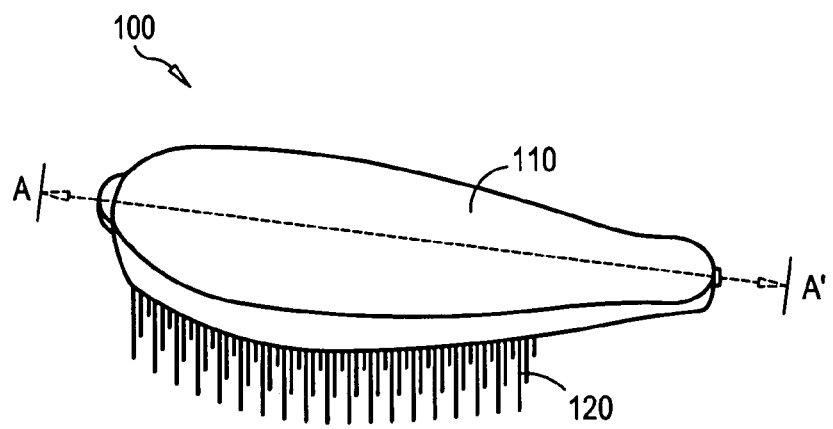
FIG. 1 illustrates an isometric top view of a hair restoration device constructed in accordance with the present invention.

Referring initially to FIG. 1, illustrated is an isometric top view of a hair restoration device 100 constructed in accordance with the present invention. The visible portions of the illustrated hair restoration device 100 are a hairbrush body 110, with bristles 120 extending from the body 110 (one of which is labeled as being representative of all). Of course those of ordinary skill in the pertinent art will understand that device 100 and hairbrush body 110 can be of any type and still be within the intended scope of the present invention. For example and without limitation, the hairbrush body 110 may or may not have a handle; the device 100 may have a flat paddle type of hairbrush body 110; the device 100 can be round, square oblong; or any other type or shape, all of which will be within the intended scope of the present invention.

Figure 2:
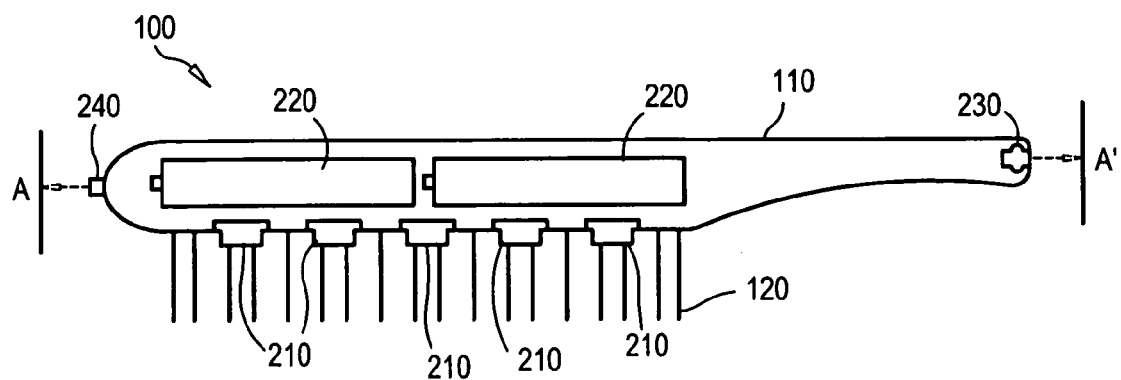
FIG. 2 illustrates a cross sectional view of the hair restoration device illustrated in FIG. 1.

FIG. 2 illustrates a cross sectional view A-A' of the hair restoration device 100 illustrated in FIG. 1. The illustrated device 100 has a plurality of wide-pattern laser LEDs 210 housed within the hairbrush body 110, as well as a battery power supply 220 used to operate the laser LEDs 210. Also shown is a charger connection 230 for use in recharging the battery power supply 220 by plugging in a recharging device (not shown) connected to an appropriate power source. The device 100 has a power switch 240 at one end, enabling a user to turn the laser LEDs 210 in the device 100 on and off.

Figure 3:
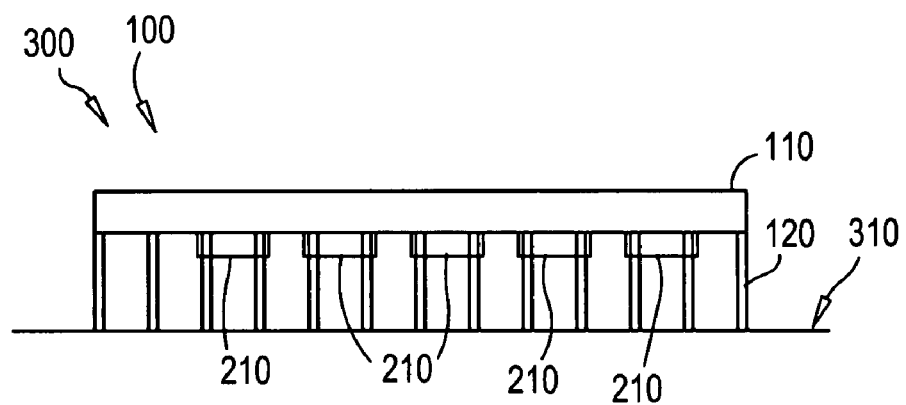
FIG. 3 illustrates a side elevation view of a hair restoration device representative of the type illustrated in FIGS. 1 and 2.

Turning now to FIG. 3, illustrated is a side elevation view 300 of a hair restoration device 100 representative of that illustrated in FIGS. 1 and 2. FIG. 3 shows a hairbrush body 110 with a single row of bristles 120 (an actual device 100 may have a single row or several such rows) and a plurality (in this instance, five) of laser LEDs 210.

Figure 4:
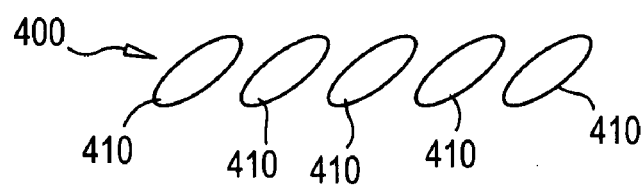
FIG. 4 illustrates a precision laser light pattern produced by a hair restoration device with an array of five wide-pattern laser LEDs.

Turning now to FIG. 4, illustrated is a precision laser light pattern 400 produced by a hair restoration device 100 with an array of five wide-pattern laser LEDs 210. In this instance, the laser light shape 410 emitted by each laser LED 210 forms is elliptical when focused on the surface on which it is projected. Of course, existing technology will permit a variety of different laser light shapes 410 to be formed by a variety of different laser LEDs 210, all of which are well within the intended scope of the present invention.

FIG. 4 illustrates a particularly useful embodiment because the laser LEDs are arranged in the hairbrush body 110 so that each elliptical laser light shape 410 is projected to appear diagonal to the major axis of the hairbrush body 110. The various laser light shapes 410 combine to cooperatively form a precision light pattern 400. Such a precision light pattern 400 permits a user to pass the hair restoration device 100 over an area of scalp or skin to be irradiated and obtain complete coverage without any gaps or holes.

To obtain laser light shapes 410 of a requisite size necessary to form a precision laser light pattern 400 and, at the same time, assure that the appropriate amount of laser energy is provided to stimulate the area to be irradiated, it is necessary that the laser light emitted by the laser LEDs 210 be focused on a specific focal plane 310 proximate the area to be irradiated. Because the tips of the bristles 120 will be in contact with the user's skin or scalp, it is desirable for the laser light pattern 400 to be focused at a focal plane that coincides closely to the tips of the bristles 120. This will also mean that, when the device 100 is used, the focal plane 310 of the laser light pattern 400 will be proximate to the skin or scalp area being irradiated. Thus, the present invention provides for bristles 120 extending from the hairbrush body 110 that terminate substantially at a focal plane 310 that will be proximate to the skin or scalp area to be irradiated.

It is not necessary for the focal plane 310 to terminate precisely at the skin or scalp area to be irradiated, because the laser light pattern 400 is designed with sufficient overlap to account for individual user variations as to the angle the device 100 is held as it is passed over the scalp or skin or the pressure placed on the device 100. Thus a typical user applying normal pressure to the device 100 will have the focal plane 310 located proximate to his or her scalp or skin and obtain full coverage, while, at the same time, a more aggressive user applying more pressure will still get full coverage because the laser light shapes 410 overlap in the laser light pattern 400.

In one embodiment of the invention, the bristles 120 are stiff to make it easier for a user to maintain the focal plane 310 on the scalp or skin being irradiated. It should be noted, however, that even very stiff bristles 120 will have some degree of flexibility. In some embodiments of the invention the bristles 120 will be softer than in others. A person of ordinary skill in the pertinent art will be able to ascertain how much pressure an average user will put on the device 100 as it is passed over the scalp and position the focal plane 310 so that it will terminate at the end of the bristles 120 as they are compressed by contact with a users scalp.

The present invention thus provides for a compact, lightweight, easy-to-use, safe hair restoration device 100 that permits a person to use it at times of his or her own choosing. A user no longer has to rely on going to a treatment center where laser irradiation has traditionally been administered or to pay the cost of such treatments. All the user needs to do is switch on the array of laser LEDs 210 and use the device as he or she would a normal hairbrush to receive appropriate and proven laser stimulation that promotes hair growth and restores hair color.

As illustrated in one embodiment, the wide pattern laser LEDs 210 project elliptical shapes 410 on the focal plane 310. Laser LEDs 210 can also project light shapes that are round, square, diamond, as well as others and still be within the intended scope of the present invention. Likewise, the illustrated hair restoration device 100 is depicted with a single row of five laser LEDs 210 arranged to form a precision light pattern 400. Those of ordinary skill in the relevant art will recognize that any number of laser LEDs 210 can be used to produce a precision laser light pattern 400 and still be within the intended scope of the present invention. The laser LEDs 210 can also be arranged in the hairbrush body 110 in a number of ways to produce precision light patterns 400, all of which arrangements are well within the intended scope of the present invention.

Although the hair restoration device 100 can be constructed from any material and be within the intended scope of the present invention, plastic is a particularly useful material to use to make the hairbrush body 110. Therefore, the invention provides for one of the embodiments to have a plastic hairbrush body 110. Plastic provides a lot of advantages, including light weight, ease of manufacture, and electrical non-conductivity.

Figure 5:
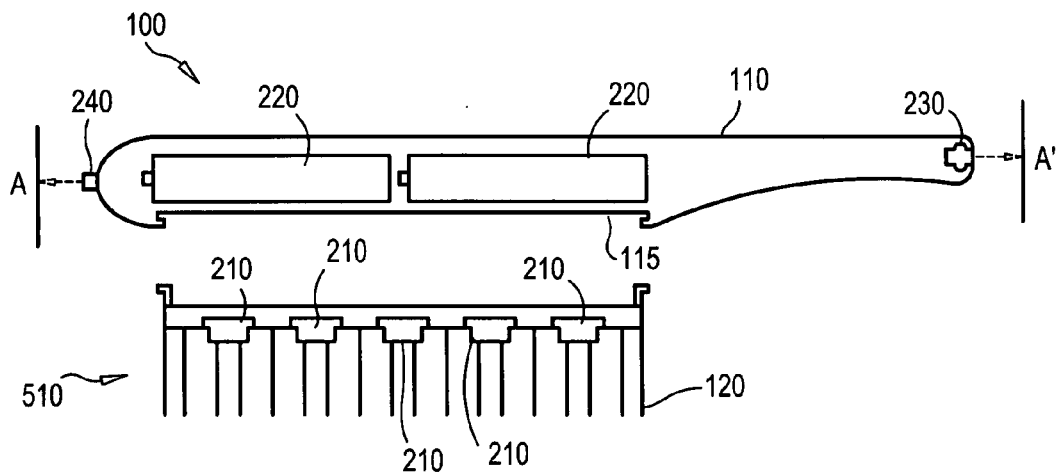
FIG. 5 illustrates a cross sectional view of the hair restoration device illustrated in FIG. 2, with an interchangeable LED head.

Turning now to FIG. 5, illustrated is a cross sectional view of the device illustrated in FIG. 2 with an interchangeable LED head 510. This embodiment is particularly useful in that it permits many different types of LED heads 510 to be used with a single device 100. The interchangeable LED head 510 is sized to be received by a cavity 115 formed in a bottom of the single device 100. For example, one LED head 510 may be used to house oval shaped LEDs or laser LEDs 210 arranged as an array to provide complete coverage of an area to be irradiated, while another interchangeable LED head 510 may have a several LEDs or laser LEDs 210 projecting a different shaped light to provide the necessary coverage of the area to be irradiated. Interchangeable LED heads 510 can also be used to provide for many types of light treatments, such as infra-red or ultraviolet treatments. By used an LED head 210 with non-laser LEDs 210 that project light having an infra-red or an ultraviolet light, a single device 100 having interchangeable LED heads can be used to provide a whole range of light treatments. In some embodiments, the wavelengths of the light projected by the LEDs can be within a range of about 235 nanometers to about 1180 nanometers.

Figure 6:
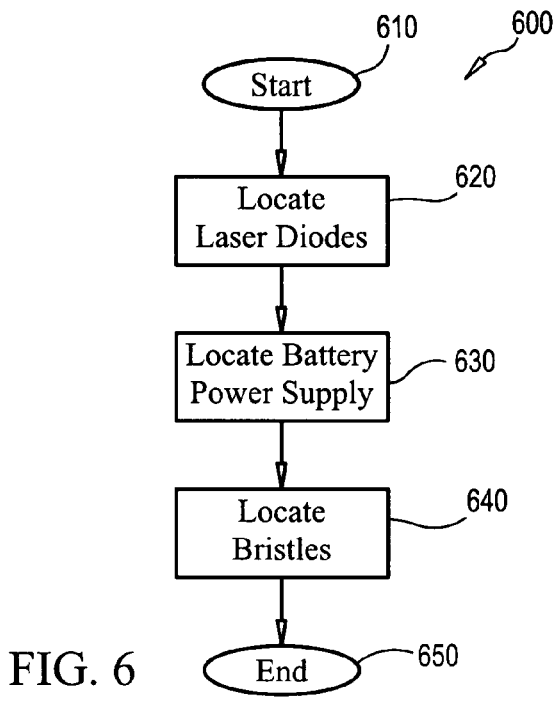
FIG. 6 illustrates a flow chart of one embodiment of a method of manufacturing a hair restoration device.

Turning now to FIG. 6, illustrated is a flow chart of one embodiment of a method 600 of manufacturing a hair restoration device. The method commences with a start step 610. In a locate laser LEDs step 620, a plurality of wide-pattern laser LEDs are located within a hairbrush body. The laser LEDs are arranged and configured to cooperatively project a precision laser light pattern at a focal plane proximate a scalp or skin area to be irradiated. In one embodiment, the laser light shapes produced by the laser LEDs are elliptical. In another embodiment, the wide-pattern laser LEDs are arranged in the hairbrush body so that each laser LED projects an elliptical laser light shape diagonal relative to the hairbrush body.

In a locate battery power supply step 630, a battery power supply is installed in the hairbrush body. In another embodiment, the power supply is rechargeable.

In a locate bristles step 640, bristles are located on the hairbrush body to extend from the hairbrush body and terminate substantially at the focal plane proximate to the skin or scalp of a user when the device is being used. In one embodiment, the bristles are stiff to assist in keeping the focal plane at the desired distance from the laser LEDs when the device is in use.

The method of manufacture concludes with an end step 650. In one embodiment of a method of manufacture, the hairbrush body is plastic. Of course the hairbrush body may be made of any material or substance and still be within the scope of the intended invention.

The invention also provides for several embodiments for a method of using a hair restoration device of the type described herein. These embodiments will be readily apparent to those of ordinary skill in the pertinent art from the foregoing disclosure.

Although the present invention has been described in detail, those skilled in the art should understand that they can make various changes, substitutions and alterations herein without departing from the spirit and scope of the invention in its broadest form.

What is claimed is:

1. A method of using a hair restoration device, comprising:
   moving a hairbrush over a skin area to be irradiated, wherein said hairbrush includes:
   a hairbrush body housing a plurality of LEDs or laser diodes configured to cooperate to project a light pattern at a focal plane proximate said skin area, said plurality of LEDs or laser diodes each projecting a light shape being diagonal to a major longitudinal axis of said hairbrush body; and
   bristles extending from said hairbrush body and terminating substantially at said focal plane.

2. The method of using a hair restoration device as recited in claim 1 wherein each of said LEDs or laser diodes projects a laser light shape that is an ellipse.

3. The method of using a hair restoration device as recited in claim 1 wherein said plurality of LEDs or laser diodes being retained in an interchangeable head.

4. The method of using a hair restoration device as recited in claim 1 wherein said LEDs or laser diodes are powered by a battery power supply housed within said hairbrush body.

5. The method of using a hair restoration device as recited in claim 4 wherein said battery power supply is rechargeable.

6. A hair restoration device, comprising:
- a hairbrush body housing a plurality of LEDs or laser diodes configured to cooperate to project a light pattern at a focal plane proximate a skin area to be irradiated, said plurality of LEDs or laser diodes projecting a light shape being diagonal to a major longitudinal axis of said hairbrush body; and
- bristles extending from said hairbrush body and terminating substantially at said focal plane.

7. The hair restoration device as recited in claim 6 wherein each of said LEDs or laser diodes projects a light shape that is an ellipse.

8. The hair restoration device as recited in claim 6 wherein said LEDs or laser diodes are powered by a battery power supply housed within said hairbrush body.

9. The hair restoration device as recited in claim 8 wherein said battery power supply is rechargeable.

10. The hair restoration device as recited in claim 6 wherein said LEDs or laser diodes emit light having a wavelength of between about 235 nanometers and about 1180 nanometers.

11. The hair restoration device as recited in claim 6 wherein said plurality of LEDs or laser diodes being retained in an interchangeable head.

12. A laser restoration device, comprising: a body housing a plurality of laser diodes configured to cooperate to project a light pattern at a focal plane proximate a skin area to be irradiated, said plurality of laser diodes projecting a laser light shape that is an ellipse, said plurality of laser diodes being diagonal to a major longitudinal axis of said hairbrush body.

13. The laser restoration device as recited in claim 12 wherein said laser diodes are powered by a battery power supply housed within said body.

14. The laser restoration device as recited in claim 13 wherein said battery power supply is rechargeable.

15. The laser restoration device as recited in claim 12 wherein said laser diodes emit light having a wavelength of between about 235 nanometers and about 1180 nanometers.

16. The laser restoration device as recited in claim 12 wherein said plurality of laser diodes being retained in an interchangeable head.

17. A method of using a laser restoration device, comprising:
- moving said laser restoration device over a skin area to be irradiated, wherein said laser restoration device includes:
- a body housing a plurality of laser diodes configured to cooperate to project a laser light pattern at a focal plane proximate said skin area, said plurality of laser diodes being retained in an interchangeable head, each of said laser diodes projecting a laser light shape that is an ellipse, wherein each of said laser light shapes is diagonal to a major axis of said body housing.

18. The method of using a laser restoration device as recited in claim 17, further comprising bristles extending from said body and terminating substantially at said focal plane.

19. The method of using a laser restoration device as recited in claim 17 wherein said laser diodes are powered by a battery power supply housed within said body.

20. The method of using a laser restoration device as recited in claim 19 wherein said battery power supply is rechargeable.

* * * * *